United States Patent [19]
Fuchs et al.

[11] Patent Number: 6,096,226
[45] Date of Patent: Aug. 1, 2000

[54] METHOD OF COMBATING PHYTOPATHOGENIC MICROORGANISMS IN THE WATER CIRCUITS OF GREENHOUSES

[75] Inventors: Rainer Fuchs, Mömbria/Hohl; Michael Huss, Eschborn; Thomas Luy, Freigericht, all of Germany

[73] Assignee: Degussa-Huls AG, Frankfurt am Main, Germany

[21] Appl. No.: 09/274,907

[22] Filed: Mar. 23, 1999

[30] Foreign Application Priority Data

Mar. 23, 1998 [DE] Germany ............................ 198 12 591

[51] Int. Cl.$^7$ ....................................................... C02F 1/72
[52] U.S. Cl. .......................... 210/759; 210/763; 210/764; 210/807; 47/58
[58] Field of Search .................................. 210/759, 763, 210/764, 765, 805, 807, 263, 295; 47/58

[56] References Cited

U.S. PATENT DOCUMENTS 6,004,469  12/1999  Sanders et al. ........................ 210/763

FOREIGN PATENT DOCUMENTS

| | | |
|---|---|---|
| 0 361 955 A1 | 4/1990 | European Pat. Off. . |
| 4-88923 | 3/1992 | Japan . |
| 9201631 | 4/1994 | Netherlands . |
| WO 93/18799 | 9/1993 | WIPO . |
| WO 94/20424 | 9/1994 | WIPO . |
| WO 96/18761 | 6/1996 | WIPO . |

OTHER PUBLICATIONS

Database WPI, Sec. Ch. Week 9218, Derwent Publications Ltd., London, GB; Class C07, AN 92–147255, XP002106165 Abstract.

Primary Examiner—David A. Simmons
Assistant Examiner—Betsey J. Morrison
Attorney, Agent, or Firm—Pillsbury Madison & Sutro LLP

[57] ABSTRACT

The phytotoxic action of too high a concentration of peroxygen compounds such as peroxycarboxylic acids and hydrogen peroxide in the combating of phytopathogenic microorganisms, such as fusaria, in the water systems of plant irrigation systems, especially greenhouses, can be eliminated. The water is treated with a peroxycarboxylic acid solution which is brought in contact with a solid decomposition catalyst for active-oxygen compounds before the water is used for irrigation, in order to reduce the content of peroxycarboxylic acid and hydrogen peroxide. The water contacts and flows through a fixed bed of decomposition catalyst, by trickling over it or flowing through the conduits of a monolithic block coated with a decomposition catalyst such as platinum, palladium or rhodium.

12 Claims, No Drawings

METHOD OF COMBATING PHYTOPATHOGENIC MICROORGANISMS IN THE WATER CIRCUITS OF GREENHOUSES

FIELD OF THE INVENTION

The invention relates to a method of combating phytopathogenic microorganisms, especially fusaria, in the water circuits of plant systems, especially those in greenhouses, using aqueous peroxycarboxylic acid solutions containing hydrogen peroxide and using a deactivator.

BACKGROUND OF THE INVENTION

Plants are planted in commercially operated plant systems, especially in greenhouses, in natural substrates such as soils, but increasingly in synthetic substrates such as, e.g., rock wool. The cultures are irrigated with water containing nutrients. Water running through the substrate and not absorbed by the plants, which is referred to herein as drainage water, is reused for irrigation.

Various microorganisms accumulate in closed water systems, which microorganisms also include phytopathogenic microorganisms, which cause the plants to die off or to be reduced in quality. Plants such as lettuces, cucumbers and chicory, and also decorative plants, are attacked to a particularly great degree by "fusarium" organisms. It has not been possible previously to entirely remove fusaria from a greenhouse area in a satisfactory manner, e.g. with the known UV treatment or thermal processes, without damaging the plants at the same time. Known processes may also be uneconomical.

Solutions containing peroxycarboxylic acid and/or hydrogen peroxide have been tested in agricultural settings in order to avoid the presence of phytotoxic microorganisms such as fungi, viruses, bacteria, yeasts and algae. According to patent DD 239 109, hydrogen peroxide is added to the irrigation water. However, the action of hydrogen peroxide for combating pathogenic organisms, especially fungi, is unsatisfactory. Moreover, the great amount of water required for use results in significant damage to the roots of the plants.

According to WO 94/20424, better results can be obtained if a solution containing performic acid is added to the drainage water or to the water used for watering. It is preferable to use a solution produced in situ from formic acid and hydrogen peroxide and containing performic acid and hydrogen peroxide. The amount required is in the range of 1 to 1000 ppm performic acid and 25 to 2500 ppm hydrogen peroxide. This method has the disadvantage that the concentrations of performic acid and hydrogen peroxide required for combating fusaria are still so great that damage to the plant roots can readily occur. The root damage due to too great a concentration of peroxide compounds can exceed the damage caused by an infection with fusarium. In general, only a concentration of around or below 30 ppm hydrogen peroxide is viewed as harmless.

The invention had the problem of providing an improved method of combating phytopathogenic microorganisms, especially fungi such as fusaria, in plant systems with an irrigation system, by which method damage to the plants is avoided.

SUMMARY OF THE INVENTION

The problem is solved by a method of combating phytopathogenic microorganisms, especially fusaria, in an irrigation system for plant systems, especially of greenhouses, which system contains drainage water and water for watering, and in which method the drainage water is treated with an aqueous peroxycarboxylic acid solution containing hydrogen peroxide and which method is characterized in that the water treated with the peroxycarboxylic acid solution is brought in contact with a solid decomposition catalyst for active oxygen compounds before it is used for irrigation in order to reduce the content of peroxycarboxylic acid and hydrogen peroxide.

The method in accordance with the invention avoids direct contact of the plants with peroxygen compounds in the high concentration that was previously necessary. The method combines an effective treatment of drainage water affected with microorganisms such as fusaria with a percarboxylic acid solution containing hydrogen peroxide and, before reuse of the water treated in this manner for irrigating the plants, the method combines posttreatment of the water rich with peroxygen compounds for reducing the peroxygen content to values which are harmless to the plants. The water posttreated in this manner to have a reduced content of $H_2O_2$ and percarboxylic acid is reused for irrigation after dilution with spring water or drinking water in order to replace the losses due to evaporation and after enrichment with nutrients.

Active oxygen compounds can be decomposed in a catalytic and biological manner using peroxidase enzymes or catalase enzymes or by chemical reaction with a reducing agent. The use of enzymes for the purpose of the invention is possible; however, the use of enzymes in greenhouses is costly as a rule and, in addition, enzyme preparations are thermally sensitive and can be preserved only in a limited fashion. Chemical decomposition, e.g. using nitrite or sulfite, is unsuitable on account of the associated concentration of salts. According to the invention the active oxygen compounds are decomposed using a decomposition catalyst.

The decomposition catalyst can be present in any solid form such as particulate form, especially in the form of granulates, extrudates, pellets or tablets, fibrous or laminate. Alternatively, the decomposition catalyst can also be arranged on the surface of conduits of a monolithic catalyst module of any shape. Finally, the decomposition catalyst can also be present as a film or thin coating on plates which for their part are arranged as a layered stack in a container, through which layered stack water can flow.

Heavy metals and their compounds from groups I, II and V to VIII of the periodic table, which metals and compounds are essentially insoluble in water are effective for decomposition. Noble metals, especially Pt, Pd and Rh as well as oxides, silicates and phosphates of iron and manganese such as magnetite and manganese dioxide are especially effective. Heavy metals or their compounds which are sufficiently stable in the environment of the drainage water are preferred. The pH of the water treated with the percarboxylic acid solution has an effect on the rate of decomposition of the active oxygen compounds. The rate of decomposition increases as the pH increases. The pH can be brought, if required, to the desired value before the treatment. The heavy metals and their compounds cited as effective for decomposition can be present per se or carrier-bound. Noble metals are preferably used bound to a carrier, namely, on a particulate carrier or on the surface of laminar carriers such as the monoliths or plate stacks cited above. Suitable carriers are known in the catalyst art. Oxides, mixed oxides, silicates, phosphates and nitrides, glasses and ceramic materials can be used, by way of example. Another class of carriers are inorganic polymers such as zeolites and organic polymers such as cation exchangers as well as activated carbon, which can also be effective for decomposition without the additionally applied heavy metals.

The use of activated carbon, with or without additional loading or charging with heavy metals, is less advantageous because as the time of use increases the effectiveness and stability of activated carbon granulates decreases.

According to a preferred embodiment, a particulate decomposition catalyst in the form of a fixed bed is arranged in a container. The drainage water can be conducted in a flooded state over the catalytic bed. Alternatively, the drainage water can also be allowed to trickle over the fixed bed so that the water only forms a film on the catalytic particles and a high efficiency including good degassing is assured.

According to a preferred embodiment, readily available catalytic monoliths with conduits coated with noble metal and known from the catalytic technology of auto exhaust can be used. The drainage water is allowed to flow through such monoliths, having a base material which is usually a ceramic material but which can also consist of other materials such as plastics, for use in the present method. Such catalysts have the advantage of a large, catalytically acting surface with a high chemical stability at the same time to all components contained in the drainage water, which components also include acids and nutrients, and cause only a slight pressure buildup.

The water is purposefully filtered before being brought in contact with the decomposition catalyst in order to separate out suspended matter and to avoid densification of the catalytic bed or clogging of the conduits of a catalytic monolith. The filtration can take place immediately before or after the treatment of the drainage water with the percarboxylic-acid solution containing $H_2O_2$.

Any peroxycarboxylic acids with 1 to 6 C atoms and one or two peroxy groups can be used to combat fusaria and other microorganisms. Mono- and diperoxycarboxylic acids with 2 to 6 C atoms and, in addition, one or two hydroxyl groups can also be used. Examples are performic acid, peracetic acid, perpropionic acid, mono- and diperoxysuccinic acid, mono- and diperoxyglutaric acid, peroxylactic acid, peroxyglycolic acid and peroxytartaric acid. Solutions containing peracetic acid and/or performic acid are preferred. The solutions used still contain hydrogen peroxide and, if applicable, a mineral-acid catalyst from the production from the corresponding carboxylic acid(s). So-called equilibrium solutions or solutions in the vicinity of equilibrium or solutions diluted immediately before use are preferably used. For example, commercial peracetic-acid solutions with a peracetic-acid content in a range of 1 to 40% by weight, especially approximately 5 to 15% by weight can be used. Instead of sulfuric acid the solutions preferably contain, conditioned by the production, the more environmentally compatible and less phytotoxic orthophosphoric acid, pyrophosphoric acid or polyphosphoric acid with the formula $H_{n+2}P_nO_{3n+1}$, in which n is a whole number equal to or greater than 3.

According to another preferred embodiment a combination of peracetic acid and performic acid is used to treat the drainage water. Such a solution can be readily produced in situ in that a source for formic acid selected from formic acid and water-soluble formates, especially sodium- or calcium formate, is added to an aqueous peracetic-acid solution obtainable in a known manner, especially to an equilibrium peracetic-acid solution and the solution obtained in this manner is added after a few minutes to a few hours residence time to the drainage water. In so far as a formate is added to the peracetic-acid solution it is advantageous to add the latter hypostoichiometrically relative to mineral-acid catalyst present. Such a combined peroxycarboxylic-acid solution has the advantage over the pure peroxyformic-acid solution of simple and safe production and better action on account of a longer useful stability. In contrast thereto, handling of formic acid is extremely problematic on account of its high corrosiveness—along with essentially the same effectiveness in combating microorganisms.

The amount of percarboxylic-acid solution used is measured so that the content of percarboxylic-acid in the drainage water contains 1 to 5000 ppm, preferably 10 to 1000 ppm and especially preferably 10 to 50 ppm peroxycarboxylic acid. Overdosing is less critical because decomposition of the active-oxygen compounds follows the combating of the phytopathogenic microorganisms, that is, before the water is used for irrigation.

The method of the invention permits a very effective combating of phytopathogenic pathogens such as, in particular, fusaria in the water of the water system of plant irrigation systems, especially those in greenhouses. Damaging of the plants, which often occurred in the past by too high a concentration of peroxygen compounds is avoided. The method can be readily realized with low technical expense. At the same time the method avoids clogging of the drip tubes serving for irrigation since no biofilm forms in them.

DETAILED DESCRIPTION OF THE PREFERRED EMBODIMENTS

EXAMPLE

Tomatoes were cultivated in a greenhouse with rock wool as the plant substrate. The water used for irrigation contained the required nutrients; the drainage water running off was continuously recycled during the day after adjustment of the nutrient content and supplementation by fresh water.

It was determined by pretests carried out externally that fusaria were quantitatively killed off in the drainage water running off by the addition of 1000 ppm of an equilibrium peracetic acid with a content of 5 % by weight peracetic acid and 27% by weight hydrogen peroxide with an exposure time of 5 minutes. During such a treatment the content of peracetic acid and hydrogen peroxide dropped only slightly.

The drainage water compounded with 1000 ppm of the previously cited peracetic-acid solution flowed, after having passed through a filter for separating suspended matter, through a deactivator. The deactivator consisted of five to eight cylindrical, commercial ceramic carriers (diameter 14.4 cm, length 15.2 cm) arranged in series in a container and with honeycomb-shaped conduits adjacent to each other (diameter 1.5 mm) whose walls were coated with platinum and rhodium (weight ratio 5 :1, total amount 13.1 g). The pH of the water was adjusted to various pH values. The throughput of water was 1 $m^3$/h. The water leaving the deactivator still contained the content of peracetic acid and hydrogen peroxide indicated in the table.

|  | Before deactivator |  | After deactivator |  |
| --- | --- | --- | --- | --- |
| pH | 4 | 4 | 7 | 9 |
| Peracetic acid (ppm) | 50 | 25 | 15 | 6 |

-continued

|  | Before deactivator |  | After deactivator |  |
|---|---|---|---|---|
| Hydrogen peroxide (ppm) | 270 | 190 | 130 | 80 |

The rate of decomposition can be regulated, apart from the pH, by adjusting the flow rate or the size of the deactivator or the frequency of the contact through recycling.

The water of the test, carried out at pH 7, was diluted in a customary manner with spring water (1:2), enriched with nutrients and subsequently utilized for irrigating a few test plants: The roots of the plants remained free of damage due to active oxygen compounds.

When the drainage water was treated solely in a manner not in accordance with the invention with said peracetic-acid solution and the water rich in active oxygen compounds was reused for irrigation there was significant and intolerable damage to the roots, which necessarily would have resulted in a reduction of yield.

What is claimed is:

1. A method of combating phytopathogenic microorganisms, in a water system of plant irrigation systems, which water system contains drainage water and water for watering, comprising
    treating the drainage water with an aqueous peroxycarboxylic acid solution containing hydrogen peroxide, and
    bringing the drainage water treated with the peroxycarboxylic acid solution into contact with a solid decomposition catalyst for active oxygen compounds before the water is used for irrigation, thereby reducing the content of peroxycarboxylic acid and hydrogen peroxide.

2. The method according to claim 1, comprising:
    flowing the drainage water through a fixed bed comprising a particulate decomposition catalyst.

3. The method according to claim 1, comprising:
    trickling the drainage water over a fixed bed comprising a particulate decomposition catalyst.

4. The method according to claim 1, comprising:
    flowing the drainage water to be contacted through conduits of a monolithic block, wherein walls of the conduits comprise a decomposition catalyst.

5. The method according to claim 4, wherein the decomposition catalyst forms a coating on the walls, and the decomposition catalyst comprises a noble metal selected from the group consisting of platinum, palladium and rhodium.

6. The method according to claim 1, wherein the solid decomposition catalyst is in the form of a granulate, extrudate or tablet and comprises a member selected from the group consisting of activated carbon, heavy metals, water-soluble compounds of heavy metals effective for decomposition, carrier-bound heavy metals and compounds of carrier-bound heavy metals effective for decomposition, which carriers are selected from the group consisting of inert oxides, silicates, phosphates, inorganic polymers, organic polymers and activated carbons,
    wherein the heavy metals effective for decomposition are selected from the group consisting of elements of groups I, II, V, VI, VII and VIII of the periodic table.

7. The method according to claim 6, wherein the heavy metals effective for decomposition are selected from groups VII and VIII of the periodic table.

8. The method according to claim 1, wherein the drainage water is filtered before or after treatment of the drainage water with the peroxycarboxylic acid solution.

9. The method according to claim 1, wherein the peroxycarboxylic acid comprises at least one member selected from the group consisting of peracetic acid and performic acid.

10. The method according to claim 1, comprising: adding 10 to 1000 ppm peroxycarboxylic acid to the drainage water.

11. The method according to claim 1, wherein the phytopathogenic microorganisms are fusaria.

12. The method according to claim 1, wherein the water system is a greenhouse water system.

* * * * *